(12) United States Patent
Wolinsky et al.

(10) Patent No.: US 6,331,189 B1
(45) Date of Patent: Dec. 18, 2001

(54) FLEXIBLE MEDICAL STENT

(75) Inventors: Lone Wolinsky, Ramat Gan; Arvi Penner, Tel Aviv, both of (IL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/419,980

(22) Filed: Oct. 18, 1999

(51) Int. Cl.$^7$ .......................................................... A61F 2/06
(52) U.S. Cl. ............................................................. 623/1.15
(58) Field of Search .................................. 623/1.16, 1.11, 623/1.12, 1.2, 1.34, 1.15; 606/191, 192, 195, 198

(56) References Cited

U.S. PATENT DOCUMENTS

| | | |
|---|---|---|
| 3,902,501 | 9/1975 | Citron et al. . |
| 4,531,243 | 7/1985 | Weber et al. . |
| 4,649,922 | 3/1987 | Wiktor . |
| 4,776,337 | 10/1988 | Palmaz . |
| 4,816,028 | 3/1989 | Kapadia et al. . |
| 4,830,003 | 5/1989 | Wolff et al. . |
| 4,856,516 | 8/1989 | Hillstead . |
| 4,886,062 | 12/1989 | Wiktor . |
| 4,893,623 | 1/1990 | Rosenbluth . |
| 4,969,458 | 11/1990 | Wiktor . |
| 4,994,071 | 2/1991 | MacGregor . |
| 5,019,085 | 5/1991 | Hillstead . |
| 5,080,674 | 1/1992 | Jacobs et al. . |
| 5,104,404 | 4/1992 | Wolff . |
| 5,116,365 | 5/1992 | Hillstead . |
| 5,135,536 | 8/1992 | Hillstead . |
| 5,178,618 | 1/1993 | Kandarpa . |
| 5,234,457 | 8/1993 | Andersen . |
| 5,282,824 | 2/1994 | Gianturco . |
| 5,293,879 | 3/1994 | Vonk et al. . |
| 5,306,250 | 4/1994 | March et al. . |
| 5,314,472 | 5/1994 | Fontaine . |
| 5,366,473 | 11/1994 | Winston et al. . |
| 5,383,892 | 1/1995 | Cardon et al. . |
| 5,389,106 | 2/1995 | Tower . |
| 5,421,955 | 6/1995 | Lau et al. . |
| 5,449,373 | 9/1995 | Pinchasik et al. . |
| 5,507,767 | 4/1996 | Maeda et al. . |
| 5,514,154 | 5/1996 | Lau et al. . |
| 5,527,354 | 6/1996 | Fontaine et al. . |
| 5,540,712 | 7/1996 | Kieshinski et al. . |
| 5,540,713 | 7/1996 | Schnepp-Pesch et al. . |
| 5,549,662 | 8/1996 | Fordenbacher . |
| 5,549,663 | 8/1996 | Cottone, Jr. . |
| 5,554,181 | 9/1996 | Das . |
| 5,556,413 | 9/1996 | Lam . |
| 5,591,197 | 1/1997 | Orth et al. . |
| 5,607,442 | 3/1997 | Fischell et al. . |
| 5,607,445 | 3/1997 | Summers . |
| 5,613,981 | 3/1997 | Boyle et al. . |
| 5,630,829 | 5/1997 | Lauterjung . |
| 5,632,771 | 5/1997 | Boatman et al. . |
| 5,636,641 | 6/1997 | Fariabi . |
| 5,643,312 | 7/1997 | Fischell et al. . |
| 5,653,727 | 8/1997 | Wiktor . |
| 5,681,346 | 10/1997 | Orth . |
| 5,697,971 | * 12/1997 | Fischell et al. . |

(List continued on next page.)

FOREIGN PATENT DOCUMENTS

| | | |
|---|---|---|
| 0679372 | 11/1995 | (EP) . |
| 1205743 | 9/1970 | (GB) . |

(List continued on next page.)

*Primary Examiner*—Kevin Truong

(57) ABSTRACT

The present invention is directed to a radially expandable medical stent having a chevron or "maple leaf" design geometry characterized by improved scaffolding, hoop strength and longitudinal flexibility. Also described are methods of making and deploying the stents.

38 Claims, 8 Drawing Sheets

U.S. PATENT DOCUMENTS

| | | |
|---|---|---|
| 5,718,713 | 2/1998 | Frantzen . |
| 5,725,570 | 3/1998 | Heath . |
| 5,725,572 * | 3/1998 | Lam et al. ........................... 623/1.16 |
| 5,728,158 | 3/1998 | Lau et al. . |
| 5,733,303 | 3/1998 | Israel et al. . |
| 5,735,871 | 4/1998 | Sgro . |
| 5,735,893 | 4/1998 | Lau et al. . |
| 5,741,327 | 4/1998 | Frantzen . |
| 5,755,776 | 5/1998 | Al-Saadon . |
| 5,759,192 | 6/1998 | Saunders . |
| 5,766,238 | 6/1998 | Lau et al. . |
| 5,776,161 | 7/1998 | Globerman . |
| 5,800,508 | 9/1998 | Goicoechea et al. . |
| 5,807,404 | 9/1998 | Richter . |
| 5,824,042 | 10/1998 | Lombardi et al. . |
| 5,895,406 * | 4/1999 | Gray et al. ........................... 606/198 |
| 5,897,588 | 4/1999 | Hull et al. . |
| 5,911,764 * | 6/1999 | Kanesaka et al. ................... 606/198 |
| B1 5,421,955 | 6/1995 | Lau et al. . |

FOREIGN PATENT DOCUMENTS

| | | |
|---|---|---|
| 9503010 | 2/1995 | (WO) . |
| WO 98/22159 | 5/1998 | (WO) . |

* cited by examiner

FLEXIBLE MEDICAL STENT

FIELD OF THE INVENTION

The present invention relates to implantable intravascular stents for maintaining vascular patency in humans and animals. More particularly, the present invention is directed to a balloon-expandable stent having a chevron or "maple leaf" design geometry characterized by improved scaffolding, hoop strength and longitudinal flexibility.

BACKGROUND OF THE INVENTION

This invention relates to intraluminal endovascular stenting, a method by which a prosthesis is inserted into a body tube and expanded so as to reopen a collapsed vessel wall and prevent the wall from recollapsing into the lumen. Endovascular stenting is particularly useful for arteries that are blocked or narrowed and is an alternative to surgical procedures that intend to bypass the occlusion.

Percutaneous transluminal coronary angioplasty (PTCA) is used to increase the lumen diameter of a coronary artery partially or totally obstructed by a build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A stent typically is a cylindrically shaped device formed from wire(s) or a tube and intended to act as a permanent prosthesis. A typical stent ranges from 5 mm to 50 mm in length. A stent is deployed in a body lumen from a radially compressed configuration into a radially expanded configuration that allows it to contact and support a body lumen. Optionally, a balloon of appropriate size and pressure can be used to open the lesion prior to delivery of the stent to its intended location.

The stent can be radially self-expanding, or it can be expandable by the use of an expansion device. The self-expanding stent is made from a resilient springy material while the device-expandable stent is made from a material that is plastically deformable. A plastically deformable stent can be implanted during a single angioplasty procedure by using a balloon catheter bearing a stent that has been crimped onto the balloon. The stent expands radially as the balloon is inflated, forcing the stent into contact with the interior of the body lumen thereby forming a supporting relationship with the vessel walls.

Deployment is effected after the stent has been introduced percutaneously, transported transluminally and positioned at a desired location by means of a delivery catheter. In the case of a balloon expandable stent, the delivery catheter is a balloon catheter, and the stent is deployed when the balloon is inflated. The stent remains as a permanent scaffold after the balloon is withdrawn. A balloon capable of withstanding relatively high inflation pressures may be preferable for stent deployment because the stent must be forced against the artery's interior wall so that it will fully expand thereby precluding the ends of the stent from hanging down into the channel encouraging the formation of thrombus.

Conventional angioplasty balloons fall into high, medium and low pressure ranges. Low pressure balloons are those which fall into rated burst pressures below 6 atmospheres. Medium pressure balloons are those which fall into rated burst pressures between 6 and 12 atmospheres. High pressure balloons are those which fall into rated burst pressures above 12 atmospheres. Burst pressure is determined by material selection, wall thickness and tensile strength.

Previous structures used as stents or intraluminal vascular grafts have included coiled stainless steel springs; helical wound spring coil made from shape memory alloy; expanding metal stents formed in a zig-zag pattern; diamond shaped, rectangular shaped, and other mesh and non-mesh designs. Exemplary stent devices are disclosed in U.S. Pat. No. 5,776,161 issued to Globerman, U.S. Pat. No. 5,449,373 issued to Pinchasik et al, U.S. Pat. No. 5,643,312 issued to Fischell et al., U.S. Pat. No. 5,421,955 issued to Lau et al., and U.S. Pat. Nos. 4,649,922, 4,886,062 and 4,969,458 issued Wiktor.

Problems to be overcome in stent design include (a) inadequate radial force to maintain expansion; (b) inadequate scaffolding of tissue to the wall; (c) pre-expansion longitudinal rigidity which negatively impacts on stent delivery; (d) inability to achieve a pre-expansion diameter small enough to pass through a narrow lumen; (e) in the case of balloon-expandable stents, unacceptable mechanical stress or strain levels in the expanded stent; (f) flaring of the ends of the stent during stent delivery; and (g) longitudinal shortening of the stent as a consequence of radial expansion.

Unfortunately, many of these problems result from or are exacerbated by the often conflicting goals of stent design. For example, it is desirable to have a high degree of scaffolding in the stent when the stent is expanded to its rated radial size so that the vessel wall will have uniform support. However, it is also desirable to have a small, relatively smooth delivered profile (sometimes referred to as "crimp diameter")when the stent is mounted on the catheter to permit the stent and catheter to traverse small diameter lesions. The person skilled in the art will appreciate that as a stent with a very small delivered profile expands radially its structural elements become farther apart and create openings that reduce the amount of scaffolding available to support the vessel. Such as stent may also exhibit a reduction in the outward radial forces (hoop strength) generated by the stent after expansion within the lumen. The larger window area and, therefore, inferior body lumen scaffolding reduces the effectiveness against recurring restenosis. The reduced outward forces may also be problematic if the stent does not firmly engage the wall of the lumen.

Another example of the conflicting goals of stent design involves attempts to achieve improved scaffolding and longitudinal flexibility during catheter delivery, since proper scaffolding will not be accomplished if there are few supporting structural elements. Yet the inclusion of too many structural elements results in a loss of stent flexibility in both the crimped and expanded states.

One attempt at addressing the high bending stresses/strains in a radially expandable stent is described in U.S. Pat. No. 4,830,003 (Wolff et al.) in which the stent is made of a series of generally straight wire segments welded together at their ends to form a zigzag shaped stent when expanded. By using generally straight wires, the bending stresses/strains associated with bends in an integral wire-formed stent body can be avoided. Disadvantages associated with this approach include, however, the cost of manufacturing the stents by welding. The welds also lower the allowable stress levels in the stent, thereby limiting its fatigue life and compression for delivery. Another disadvantage is that the length of the stent can change significantly from the compressed state to the expanded state, thereby making accurate placement of the stent at the desired location within a body lumen more difficult.

U.S. Pat. No. 5,776,161 issued to Globerman, which is incorporated by reference herein in its entirety, addresses a number of these issues. Globerman discloses an expandable stent having a small initial diameter, flexibility along its longitudinal axis prior to expansion and minimization of rigid local strain on the stent material by the presence of rotation joints which have minimal strain during stent expansion. The stent is substantially the same length before and after expansion and being flexible longitudinally when constrained, it is easy to deliver. However additional improvements in longitudinal flexibility in the crimped stent during delivery and scaffolding after delivery are still desired.

SUMMARY OF THE INVENTION

It is an object of the invention to provide a radially expandable stent for implantation within a body lumen having improved hoop strength and scaffolding properties.

It is another object of the invention to provide a radially expandable stent having a reduced crimp diameter while maintaining satisfactory longitudinal flexibility, scaffolding and hoop strength.

It is a further object of the invention to provide a radially expandable stent that has improved longitudinal flexibility to allow for threading through tortuous lumens and lesions, as well as to permit implantation into curved lumens.

It is another object of the invention to provide a radially expandable stent having reduced end flare.

These and other objects are achieved by the radially expandable stent of the invention, which has many advantages over known devices. The radially expandable stent of the invention exhibits improved resistance to fatigue cracking due to bending loads, improved scaffolding and hoop strength, is able to reach lesions that are otherwise difficult to access without aid of additional retention methods, and is associated with a significantly lower dislodgment rate. The radially expandable stent of the invention can be a plastically deformable device-expandable stent, such as a balloon expandable stent, or a radially self-expanding stent made from a resilient springy material.

In one aspect, the present invention provides medical device that includes a catheter and a stent mounted on the catheter, the stent being a radially expandable stent for implantation within a body lumen in the form of an elongated generally tubular body defining a passageway having a longitudinal axis. The stent is radially compressible into a compressed diameter, and radially expandable into an expanded diameter. The tubular body includes a plurality of circumferential ring elements arranged successively along the longitudinal axis of the stent, each of the ring elements having a proximal and distal end defining a longitudinal length along the longitudinal axis. Each of the ring elements includes a plurality of peaks and valleys interconnected by curved struts, the peaks and valleys being located at the proximal and distal ends of the ring element such that they are disposed circumferentially on the ring element, the struts connecting peaks and valleys on opposite ends of the ring element. The high point of a peak, and the low point of a valley, are referred to herein as peak and valley apices. The struts are curved or bent about a circumference of the stent in a fashion that allows the struts, peaks and valleys to remain generally disposed on the surface of the stent. In the compressed state, the curved struts of a ring element are arranged in a nested fashion, forming a pattern defined by the curved struts and the peaks and valleys that can be conveniently described as a "chevron" or "maple leaf" pattern. The struts can be fit together closely in a nested arrangement as the stent is crimped on the balloon catheter. By "nest," "nested," or "nesting" we mean that the elements are conformally arranged such they can be in very close proximity when the stent is crimped onto the catheter but without substantial contact that would affect the ability of the various elements to move in relation to each other as the stent and catheter are advanced through a tortuous body vessel. In a preferred embodiment, the longitudinal length of the two end rings is shorter than the longitudinal lengths of the other rings, so as to reduce end flare during advancement, delivery and transportation of the stent.

The stent further includes at least one longitudinal connection between adjacent ring elements in the tubular body. Preferably, two or three longitudinal connections occur between adjacent ring elements. Typically, less than about half of the peaks or valleys on a ring are occupied by longitudinal connections. However, the number of longitudinal connections is not intended to be limited in any way; rather, the optimal number of longitudinal connections in general is affected by the number of peaks and valleys in the rings, the diameters of the stent in the compressed form and the radially expanded form, the longitudinal length of the stent, and its intended use, among other things. A stent may contain one or more types of longitudinal connections, which can, for example, take the form of longitudinal connectors or, alternatively, integral connecting regions between a peak on one ring and a valley on an adjacent ring. Longitudinal connectors may be parallel to the longitudinal axis of the stent, or they can be offset from the longitudinal axis of the stent. It should be understood that the invention is not limited by the conformation of the longitudinal connectors or their positions of attachment to the ring elements. Longitudinal connectors can be straight or they can include, for example, one or more curved or bent segments. The longitudinal connectors are preferably arranged to prevent shortening of the stent as the stent is radially expanded. Further, longitudinal connectors are preferably arranged to promote longitudinal flexibility of the stent. For example, longitudinal connectors typically connect two adjacent ring elements and do not extend to connect additional ring elements. Thus, longitudinal connectors in successive rings are preferably "out-of-phase" with respect to each other, as defined hereinbelow, to improve the longitudinal or "bending" flexibility of the stent. The use of two or three longitudinal connectors between a pair of adjacent rings is typically preferred to achieve the greatest bending flexibility. A longitudinal connector that is curved in a compressed stent may become straight in a radially expanded stent. Alternatively, a longitudinal connector that is straight in a compressed stent may become curved in a radially expanded stent. See U.S. Pat. No. 5,776,161 issued to Globerman for examples of various longitudinal connectors.

As stents are advanced through tortuosities of a vessel, they are subjected to bending forces that can produce longitudinal stresses on the stent components. If the movements of longitudinal connectors caused by these bending forces pull the ring elements open from their crimped positions, the stent can become radially enlarged, especially at its ends (i.e., end flare) and can have difficulty crossing a narrow lesion. The present invention reduces or prevents premature radial expansion of one or more ring elements during delivery of a stent to a site in a body lumen by incorporating curves into the struts of the ring elements. The curved struts are capable of elastic longitudinal movement that promotes the tendency of the stent to flex longitudinally when it is subjected to bending forces such as those encountered during delivery of the stent and catheter through a tortuous coronary artery.

The need for spacing between the components in the crimped condition must be balanced with the need to provide effective scaffolding of the vessel being treated. In the present invention, the curved shape of the struts can provide the spacing needed for the nesting of the ring and longitudinal connector components by extending the ring in a generally circumferential direction for a distance which allows the stent to be crimped to a small diameter onto the catheter. When the stent is in its expanded state, scaffolding provided to the vessel is promoted because the struts do not fully straighten but remain partially curved in a generally circumferential direction. The slightly curved struts result in small, multi-sided cells thereby improving both scaffolding and hoop strength. Because of their irregular shape, these nonrectangular cells allow a smaller portion of the vessel wall to protrude through the opening than would be allowed by square cells having a similar perimeter or surface area, resulting in better scaffolding. A typical expansion ratio for a radially expandable stent of the invention is about 2.5 to about 3.0 but can be up to about 6.0. Moreover, the curved shape of the struts decreases the risk of dislodgement of the compressed balloon-expandable stent as it is being delivered, relative to a comparable stent with straight struts. Within a ring of a stent of the invention, each strut forms a V-shaped curve that is symmetrical about a circumference of the stent. The "V" thus points in a circumferential direction. When the stent is crimped onto the balloon, the V-shaped curve opposes longitudinal movement of the stent relative to the balloon due to the edges of the strut having a slightly circumferential orientation.

Various embodiments of the medical device of the invention further include one or more of the following features: (a) a chevron pattern in one ring element of the stent that is "in-phase" with the chevron pattern in an adjacent ring element of the stent; (b) a chevron pattern in one ring element of the stent that is "out-of-phase" with the chevron pattern in an adjacent ring element of the stent; (c) a chevron pattern in one ring element of the stent that is "in-phase" with the chevron pattern in one adjacent ring element and "out-of-phase" with the chevron pattern on the other adjacent ring element of the stent; (d) a chevron pattern in one ring element of the stent that is parallel to the chevron pattern in an adjacent ring element of the stent; (e) a chevron pattern in one ring element of the stent that is antiparallel to the chevron pattern in an adjacent ring element of the stent; (f) a chevron pattern in one ring element of the stent that is parallel to the chevron pattern in one adjacent ring element of the stent and antiparallel to the chevron pattern in the other adjacent ring element of the stent; (g) longitudinal connectors connecting the apex of a peak in one ring element of the stent to the apex of a valley in an adjacent ring element of the stent; (h) longitudinal connectors connecting a strut of one ring element of the stent with a strut of an adjacent ring element of the stent; (i) longitudinal connectors that are curved or bent in both the compressed and expanded stent profile; (j) longitudinal connectors that are straight in both the compressed and expanded stent profile; (k) longitudinal connectors that are curved or bent in the compressed stent profile and straight in the expanded stent profile; (l) longitudinal connectors that are straight in the compressed stent profile and curved or bent in the expanded stent profile; (m) ring elements made from a single elongated member that snakes around the circumference of tubular body; (n) ring elements comprising a plurality of connected, closed structures; (o) ring elements having circumferentially successive peaks and valleys alternately located on the ends of the ring element around the circumference of the tubular body; (p) ring elements having pairs peaks and valleys disposed at the distal and proximal ends of the ring element along a line parallel to the longitudinal axis of the stent; (q) at least two ring elements having different longitudinal lengths; and (r) at least one end ring element fashioned so as to accommodate a radiopaque marker. The terms "in-phase," "out-of-phase," "chevron," "parallel," and "anti-parallel" are defined or expanded upon below.

In another aspect, the present invention provides a method for using a radially expandable stent of the invention. The method includes advancing the distal end of a delivery device and the stent through a body lumen, followed by deploying the stent at a desired location within the body lumen.

In yet another aspect, the present invention provides a method of making a radially expandable stent of the invention. The stent can be made from a tube that is cut with lasers or other techniques that are well known to those skilled in the art. The initial pattern cut into the tube includes longitudinal connector and ring components that cooperate with each other. Sufficient spacing is provided between the stent components to allow the stent to be crimped onto a catheter without causing general abutment of the ring and longitudinal connector components with each other, thereby permitting bending of the stent without disturbing the crimp of the ring components on the catheter during deployment of the stent through tortuous coronary arteries.

These and other features and advantages of the present invention are described below in connection the description of the preferred embodiments.

DETAILED DESCRIPTION OF THE PREFERRED EMBODIMENTS

Figure 1:
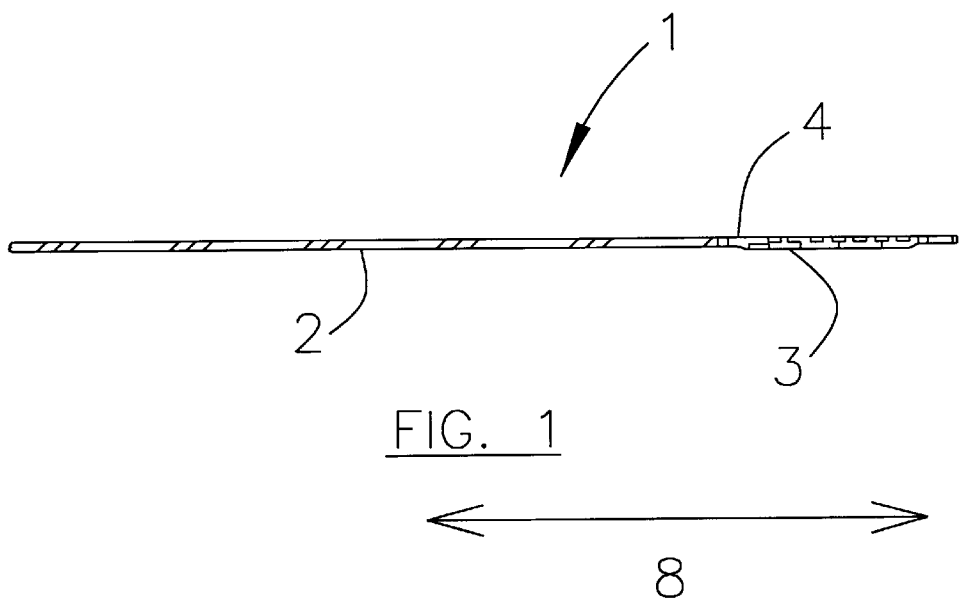
FIG. 1 is an elevational view of a balloon catheter with a stent mounted on the balloon portion of the catheter.

Referring now to FIG. 1, the medical device 1 of the present invention includes a catheter 2 and a stent 3 mounted on the catheter 2 in an unexpanded condition. Stent 3 has a hollow, cylindrical body made with a plurality of rings about a longitudinal axis 8. As shown, stent 3 is crimped over a balloon 4 affixed to catheter 2 near the distal end of catheter 2. Stent 3 can include a variety of configurations as depicted in FIGS. 2–5 which are shown in an open and flattened configuration as they would appear in an unexpanded and uncrimped condition. Balloon 4 can be practically any balloon suitable for angioplasty procedures and capable of inflation to 6 atmospheres or more of pressure. A preferred type of balloon 4 is a balloon with multiple folds that permits the stent to expand evenly that is approximately the same length as the stent. In addition to crimping, stent 3 can be held onto balloon 4 by retention techniques that are well known to those skilled in the art.

Figure 2:
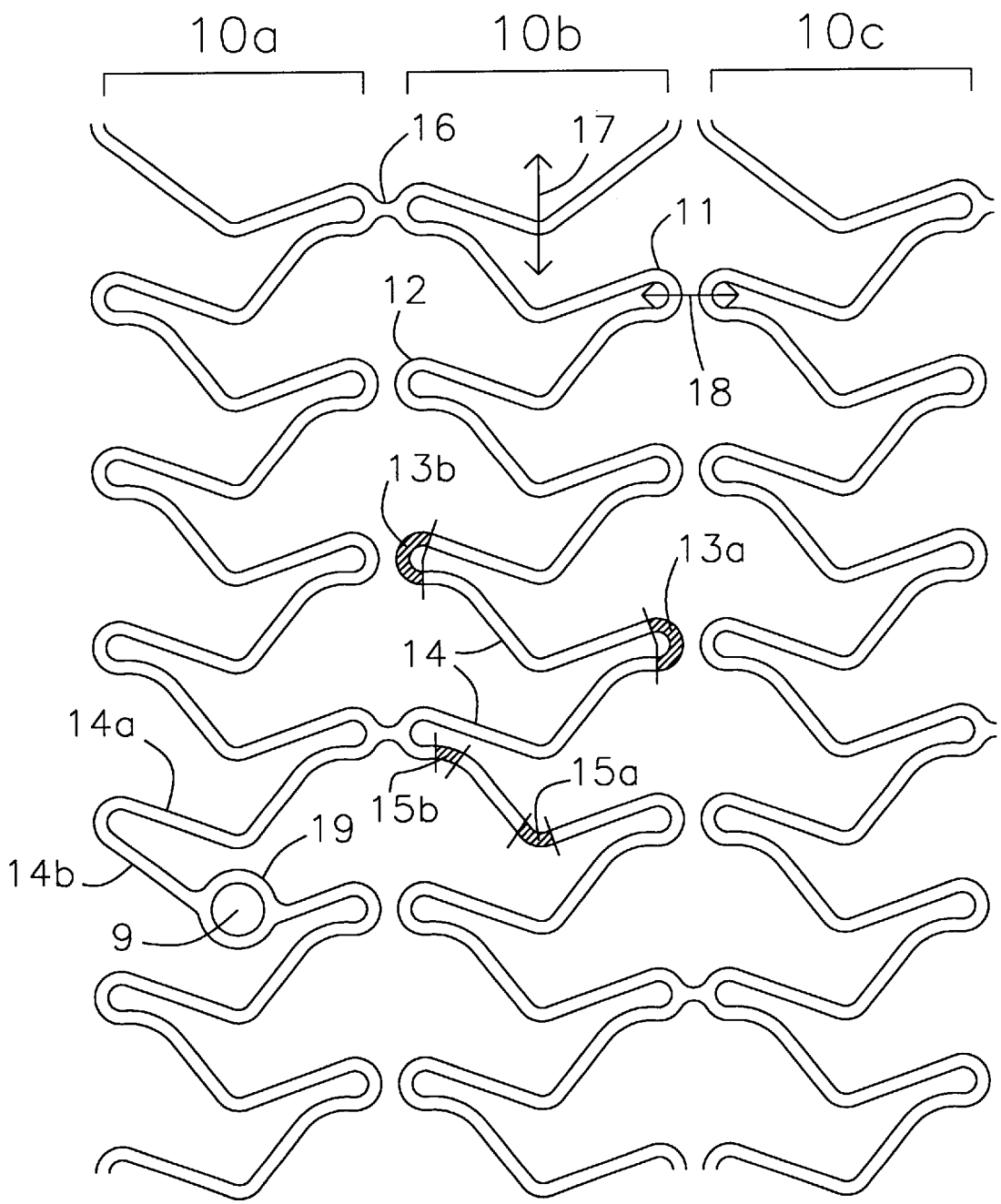
FIGS. 2–4 are flattened plan views showing portions of stents made according to the present invention. Each of the stent patterns shown would be curved into a cylindrical shape and crimped onto the balloon catheter as shown in FIG. 1.

Referring now also to FIG. 2, each of rings 10a–c extends circumferentially around the cylindrical body of stent 3 and includes an undulating series of peaks 11 and valleys 12. The undulating peaks 11 and valleys 12 of the rings 10a–c are formed by opposing curved peak and valley segments 13a–b joined to each other by struts 14. Struts 14 also contain two opposing curved segments 15a–b. As shown in FIG. 2, first curved strut segment 15a is positioned in a central portion of strut 14, and second curved strut segment 15b is positioned near or adjacent to valley curved segment 13b. First curved strut segment 15a is substantially symmetrical about a line 17 perpendicular to longitudinal axis 8 of stent. Curved strut segment 15a allows nesting of the struts within a ring and promote longitudinal flexibility as the stent is delivered on the catheter; curved strut segment 15b further facilitates nesting so as to achieve an even smaller crimp diameter. The irregularly-shaped cells defined by peak and valley segments 13a–b and curved struts 14 also provide effective scaffolding after deployment. As is readily apparent from the overall stent design of FIG. 2, struts 14 alternate circumferentially around rings 10a–c, such that for every other strut 14, the second curved strut segment 15b is positioned near or adjacent to curved peak segment 13a rather than curved valley segment 13b. The resulting shape of individual peaks 11 and valleys 12 is that of an asymmetrical hairpin. Because of the alternating nature of the peaks 11 and valleys 12 connected by struts 14, the configuration of each ring 10a–c is that of a continuous modified zigzag. Furthermore, as a result of the conformal nesting within a given ring 10a–c of struts 14, the zigzag pattern is curved about a circumference of stent 3 to form a chevron or nested "V"-shaped pattern. In relation to each other, successive rings 10a–c shown in FIG. 2 are in a parallel chevron pattern. The parallel chevron pattern in the plan view of FIG. 2 results from the conformal nesting of all struts 14 on each of rings 10a–c in a single uniform circumferential direction (i.e., either all struts 14 nest in a clockwise direction, or all struts 14 nest in a counterclockwise direction). Further, in the configuration shown in FIG. 2, rings 10a–c are oriented such that each ring is a mirror image of the ring(s) adjacent to it. Undulating peaks 11 and valleys 12 of rings 10a–c are thus arranged such that peaks 11 of ring 10a are longitudinally aligned with valleys 12 of ring 10b. As the term is used herein, two or more components of stent 3 are "longitudinally aligned" if a line (e.g., line 18 in FIG. 2) drawn through the components is substantially parallel to the longitudinal axis 8 of stent 3. It should be noted that the invention is not limited by the orientation of a ring relative to an adjacent ring; i.e., rings 10a–c can be arranged to be mirror images to each as shown in FIG. 2, or to pair peaks 11 and valleys 12 with each other in an "in-phase" relationship, as described in more detail below with reference to FIG. 3, or to make any alignment of the rings intermediate to those positions.

Continuing to refer to FIGS. 1 and 2, rings 10a–c are shown joined together by two short, substantially straight longitudinal connectors 16. In the configuration shown in FIG. 2, longitudinal connectors 16 are parallel to the longitudinal axis 8 of stent 3 and connect adjacent rings 10a–c at the apices of longitudinally aligned peak and valley pairs 11/12. The number of longitudinal connectors 16 between two adjacent rings is preferably two or three but can be more. Preferably, no more than one longitudinal connector 16 is connected to a peak 11 or a valley 12. A longitudinal connector 16 that extends between a first ring and an adjacent second ring does not extend to a third ring. This design feature renders the points of connection between a longitudinal connector 16 and a peak 11 or a valley 12 "dead ends" in the longitudinal extent of the longitudinal connectors 16 for the stent 3 and permits transfer of the flexing forces from the short straight longitudinal connectors 16 to the curved strut segments 15a and 15b. The curved struts thus absorb the bending forces transferred by longitudinal connectors 16 that are short and/or stiff. Because they are straight and connect longitudinally aligned peak and valley pairs 11/12, longitudinal connectors 16 can be quite short, for example about 0.1 mm in length. Short longitudinal connectors provide improved scaffolding. However, longitudinal connectors 16 must still be long enough to prevent interference between peak and valley apices of adjacent rings. A radiopaque marker 9 is joined to ring 10a inside a circular land portion 19 located a central portion of strut 14b. Struts 14a and 14b are shaped such that radiopaque marker 9 will not interfere with the ring as the stent 3 is crimped onto the balloon 4 of catheter 2.

Figure 3:
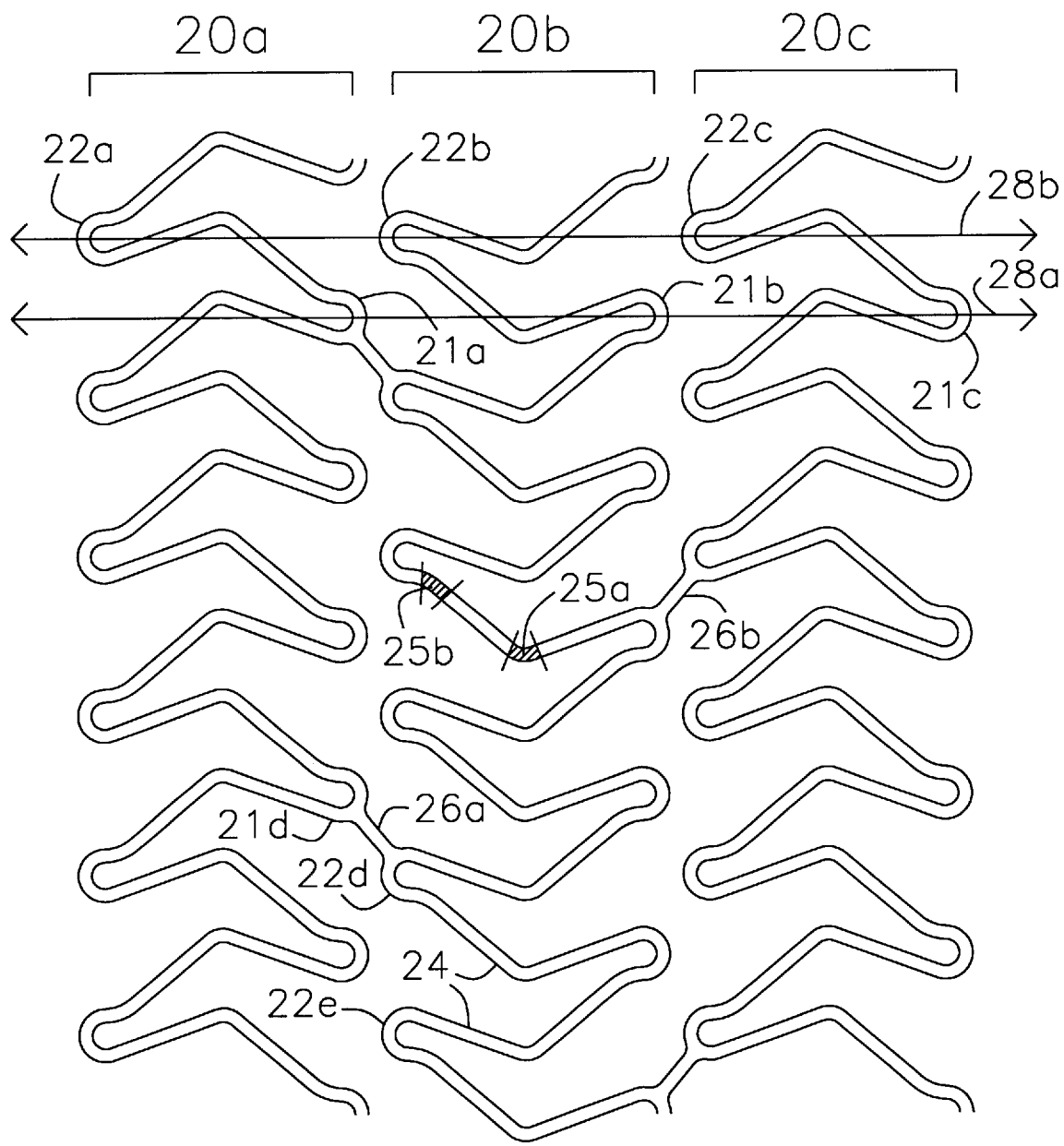

Referring now to FIGS. 1 and 3, in another embodiment of the invention, successive rings 20a–c are arranged in an antiparallel chevron configuration with respect to each other. The antiparallel chevron pattern in the plan view of FIG. 3 results from the alternating nature of the conformal nesting direction of struts 24 on successive rings 20a–c. Specifically, struts 24 of ring 20a and 20c nest in a counterclockwise circumferential direction, while struts 24 of ring 20b nest in a clockwise direction, generating the antiparallel chevron pattern. Further, in the embodiment shown in FIG. 3 peaks 21 and valleys 22 of successive rings are paired with each other in an in-phase relationship, although as described previously the stent design is not limited by the relative orientation of one ring relative to its adjacent ring(s). Line 28a drawn through peaks 21a–c is substantially parallel to longitudinal axis 8 of stent 3. Likewise, line 28b drawn through valleys 22a–c is substantially parallel to longitudinal axis 8 of stent 3. Peaks 21 a–c of rings 20a–c are thus longitudinally aligned with one another; likewise valleys 22a–c of rings 20a–c are longitudinally aligned with one another, thereby defining the in-phase relationship among the rings. Rings 20a–c are shown joined together two short, substantially straight longitudinal connectors 26. In the configuration shown in FIG. 3, longitudinal connectors 26 are not parallel to the longitudinal axis 8 of stent 3, but instead are necessarily offset with respect thereto because the peak and valley pairs 21/22 that they connect are not longitudinally aligned as they would be in a mirror image configuration as shown in FIG. 2. In the in-phase ring configuration shown in FIG. 3, peak 21d of ring 20a is defined as being "circumferentially adjacent" to valleys 22d and 22e of ring 20b. Likewise, peak 21b of ring 20b is circumferentially adjacent to valleys 22c and 22f of ring 20c. Longitudinal connector 26a connects peak 21d on ring 20a and circumferentially adjacent valley 22d on ring 20b, is substantially parallel to struts 24 associated with peak 21d and valley 22d. Likewise, longitudinal connector 26b connects peak 21b on ring 20b and circumferentially adjacent valley 22c on ring 20c, and is substantially parallel to struts 24 associated with peak 21b and valley 22c. Preferably, no more than one longitudinal connector 26 is connected to a peak 21 or a valley 22. As in the stent design of FIG. 2, a longitudinal connector 16 that extends between a first ring and an adjacent second ring does not extend to a third ring. This design feature renders the points of connection between a longitudinal connector 26 and a peak 21 or a valley 22 "dead ends" in the longitudinal extent of the longitudinal connectors 26 for the stent 3 and permits transfer of the flexing forces from the short straight longitudinal connectors 26 to the curves strut segments 25a and 25b. Because they are straight and connect circumferentially adjacent peak and valley pairs 21/22, longitudinal connectors 26 can be quite short, as described for FIG. 2.

Figure 4:
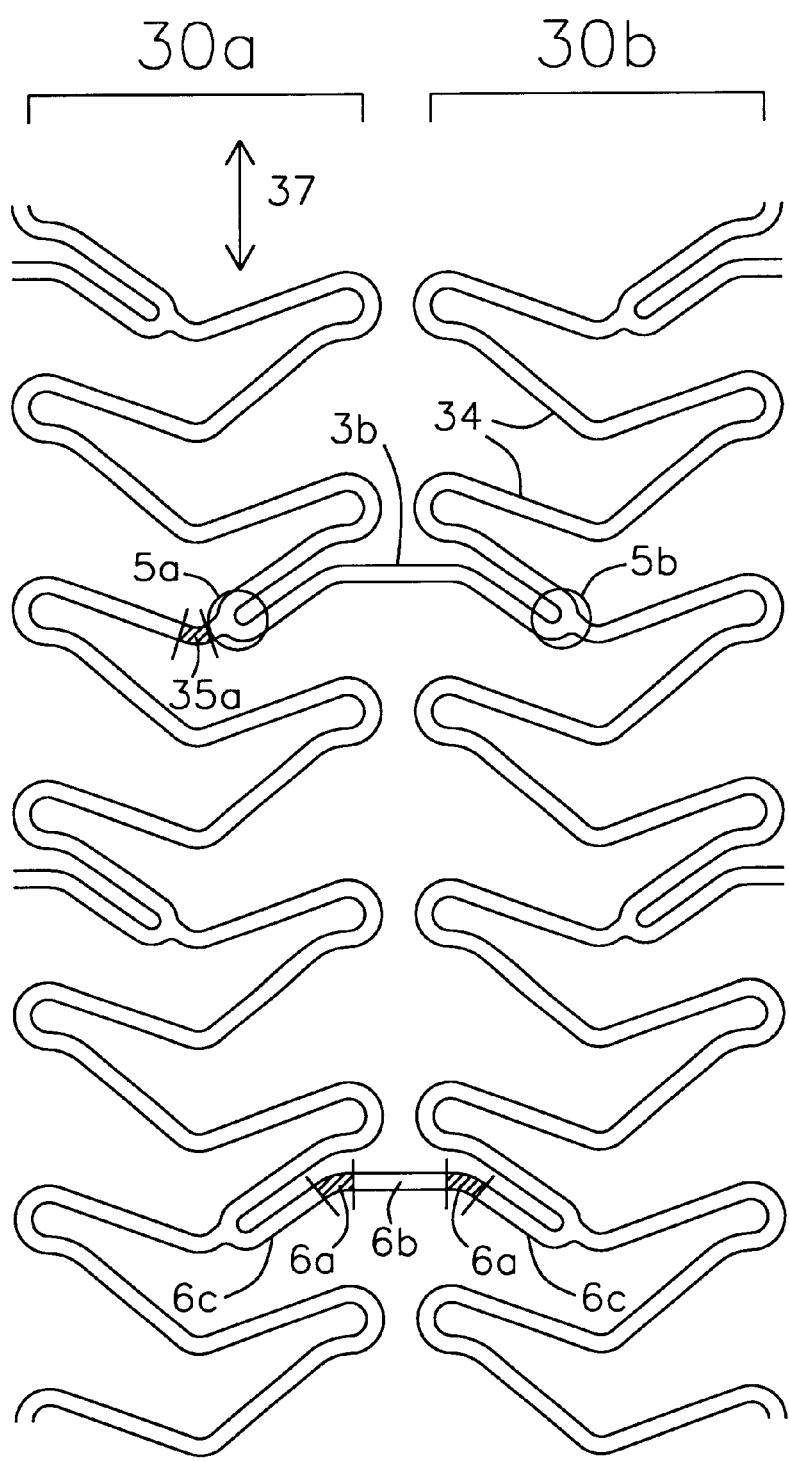

Referring now to FIGS. 1 and 4, in yet another embodiment of the invention, successive rings 30a–b are arranged in a parallel chevron configuration with respect to each other and are oriented as mirror images of each other, as in FIG. 2. Rings 30a–b are provided with inflection points 5 on some struts 34. Inflection point 5 is positioned near first curved strut segment 35a, curved strut segment being positioned in a central portion of strut 34. At each inflection point 5, a portion of the ring extends in a generally circumferential direction (indicated generally 37) for a short distance. Longitudinal connector 36 is joined at one end at the inflection point 5a on one ring 30a and also joined at a second end at a second inflection point 5b on an adjacent ring 30b. Inflection points 5a and 5b are longitudinally aligned with one another. Extending a longitudinal connector between the central portions of struts on adjacent rings has certain advantages over extending the longitudinal connector between peak and valley apices on adjacent rings. The stent is less likely to shorten as it is radially expanded, is more longitudinally flexible in both its radially compressed state and its expanded state, and provides better scaffolding. On the other hand, because longitudinal connectors that are centrally positioned on struts typically contain more metal than the short, apically positioned longitudinal connectors, their presence may interfere with crimping of the stent to the desired compressed diameter.

Longitudinal connector 36 contains two curved segments 6a. Optionally longitudinal connector 36 further contains a straight segment 6b that is substantially parallel to the longitudinal axis 8 of stent 3. Straight segment 6b keeps peak and valley apices on adjacent rings far enough apart so that they do not interfere with each other, and curved segments 6a promote nesting of the struts in the compressed form. Straight segment 6c is disposed between inflection point 5a or 5b and curved segment 6a, and is substantially parallel to strut 34. The short portion of the rings 30a–b at inflection points 5a and 5b which extends generally circumferentially has a length, measured circumferentially, which is about equal to a width of the longitudinal connector to which it is attached. This promotes the scaffolding provided to the vessel by the expanded stent 3 since the longitudinal connectors can be fit together closely in a nested arrangement with the undulations of the rings 30a–b as the stent 3 is crimped on the balloon 4 of catheter 2. Only one longitudinal connector is connected to either of the inflection points 5a–b. This makes inflection point 5 a "dead end" in the longitudinal extent of the longitudinal connectors 36 for the stent 3 and permits some of the flexing forces which are not absorbed by the longitudinal connector itself to be absorbed by the rings 30a–b to which it is attached. The number of longitudinal connectors 26 between two adjacent rings is preferably two or three.

Figure 5:
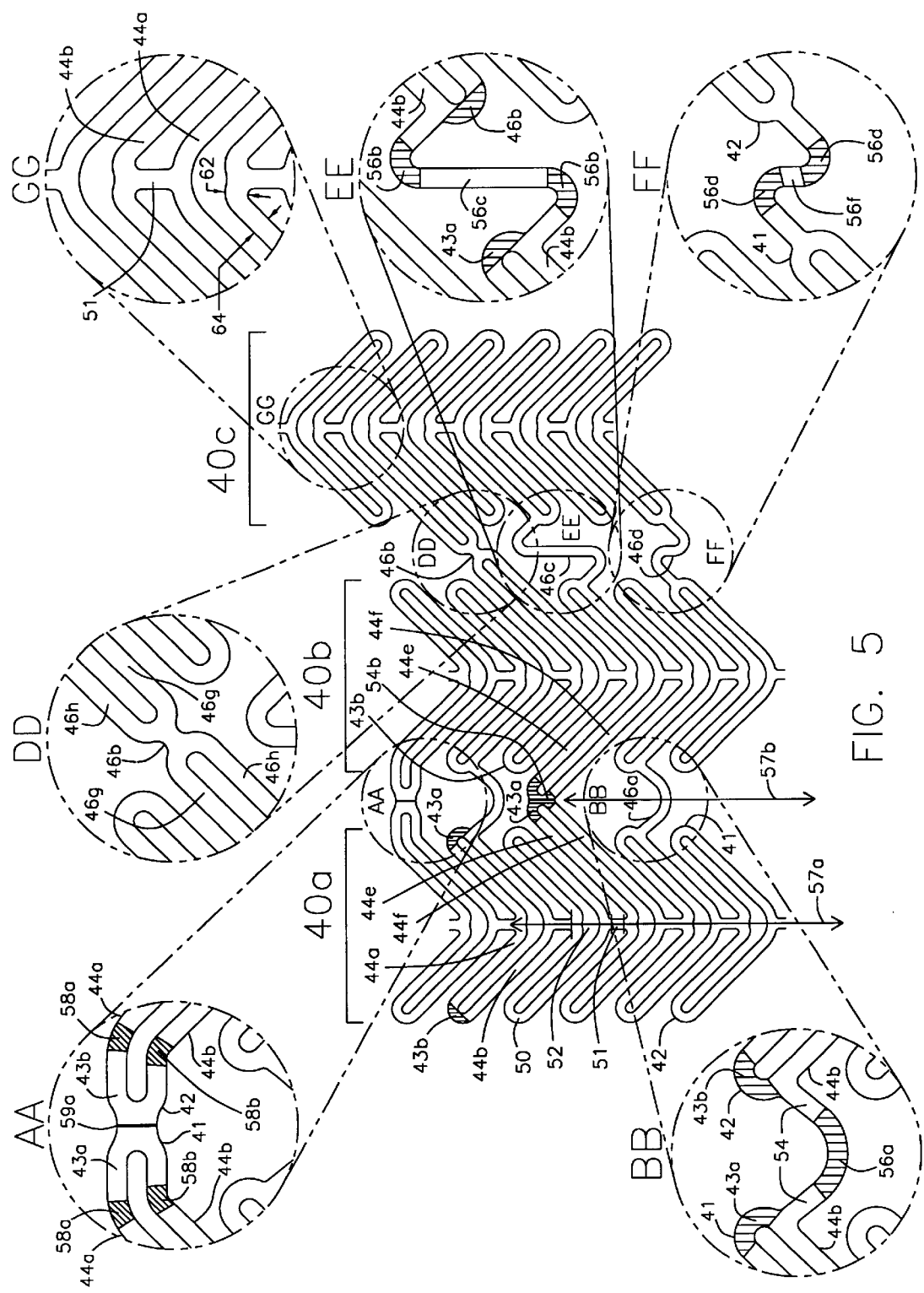
FIG. 5 is a flattened plan view illustrative of various design features of stents made according to the present invention.

Referring now to FIGS. 1 and 5, in yet another embodiment of the invention, various alternative design features of a stent 3 made according to the present invention are shown. It should be understood that FIG. 5 does not purport to show a single stent design, but rather illustrates, in a single drawing, various design features that can be utilized alone or in various combinations to make a stent 3 of the invention. For example, one or more of the means for longitudinally connecting two rings illustrated in FIG. 5 can be used to connect rings 10a–c, 20a–c and 30a–b as shown in FIGS. 2–4 to make a stent 3 of the invention.

Rings 40a–c of FIG. 5 are made from nested closed members 50 connected by short straight circumferential connectors 51. Closed members 50 are formed by opposing curved peak and valley segments 43a–b joined to each other by shorter curved strut 44a and longer curved strut 44b, defining a V-shaped interstitial space 52 that is substantially symmetric about a line 57a perpendicular to longitudinal axis 8 of stent 3. Within a ring, circumferential connectors 51 extend between shorter strut 44a and longer strut 44b of circumferentially adjacent closed members 50. Circumferential connectors 51 connect circumferentially adjacent closed members 50 at the nadir or "bottom" of the V-shape. Closed member 50 contains an indentation 60 on shorter strut 44a positioned opposite the point on strut 44a where circumferential connector 51 attaches, as shown on inset GG in FIG. 5. Indentation 60 serves to reduce the amount of metal at that junction, thereby enhancing longitudinal flexibility of the stent during delivery and reducing mechanical stress upon radial expansion of the stent. Indentation 60 is fabricated such that width 62 of longer strut 44b at indentation 60 is substantially equivalent to width 64 of a central portion of strut 44b.

Two different ring orientations are illustrated in FIG. 5. Rings 40a and 40b are disposed in a parallel chevron configuration, and rings 40b and 40c are disposed in an antiparallel chevron configuration. All three rings 40a–c are mirror images with respect to their adjacent ring(s).

Several different types of longitudinal connections are illustrated in FIG. 5. At longitudinal connection AA (see inset), parallel rings 40a and 40b are integrally connected at opposing curved peak segment 43a and curved valley segment 43b of longitudinally adjacent peak 41 and valley 42, respectively, at region 59a ; no longitudinal connector segment is used. Struts 44a and 44b contain curved segments 58a and 58b, respectively, that cause peak 41 and valley 42 to diametrically oppose each other.

At longitudinal connection BB (see inset), rings 40a and 40b are connected at longitudinally adjacent peak 41 and valley 42 by longitudinal connector 46a. One end of longitudinal connector 46a attaches to longer strut 44b of ring 40a at a location near or to curved peak segment 43a. Longitudinal connector 46a is thus attached on the "underside" of the "V" formed by closed member 50 so as not to interfere with the nested V (chevron) pattern. The other end of longitudinal connector 46a attaches to ring 40b at an analogous location on longer strut 44b near or adjacent to curved valley segment 43b of ring 40a. Longitudinal connector 46a contains a curved segment 56a positioned in a central portion thereof, flanked by two substantially straight portions 54 substantially perpendicular to longer struts 44b of closed member 50. Curved segment 56a is substantially symmetrical about a line 57b perpendicular to longitudinal axis 8 of stent 3.

At longitudinal connection CC, rings 40a and 40b are also integrally connected at opposing curved peak segment 43a and curved valley segment 43b of longitudinally adjacent peak 41 and valley 42, respectively, at region 59b. Struts 44e and 44f are longer than corresponding struts 44a and 44b to allow curved peak segment 43a and curved valley segment 43b to meet. Antiparallel rings 40b and 40c are connected by longitudinal connectors 46b –d. At longitudinal connection DD (see inset), longitudinal connector 46b is substantially straight and is parallel to struts 44g and 44h of peak 41 and valley 42; in that respect it is analogous to longitudinal connector 26b in FIG. 3. However, rings 20a–c in FIG. 3 are in-phase, whereas rings 40b–c are mirror images. If longitudinal connector 46b is short, as shown in FIG. 5, struts 44g–h must be longer than corresponding struts 44a–b. If longitudinal connector 46b is long enough (not shown), struts 44g–h can be equivalent in length to struts 44a–b.

At longitudinal connection EE (see inset), longitudinal connector 46c is attached at one end to longer strut 44b of ring 40b at a location near or adjacent to curved peak segment 43a, and at the other end to an analogous location on longer strut 44b of ring 40c near or adjacent to curved valley segment 43b. Longitudinal connector 46c includes two curved segments 56b that flank a central segment 56c that is oriented in a generally circumferential direction.

At longitudinal connection FF, longitudinal connector 46d extends between the apices of longitudinally aligned peak 41 on ring 40b and valley 42 on ring 40c, respectively. Longitudinal connector 46d includes two curved segments 56d that flank an optional central segment 56f that is oriented in a substantially circumferential direction. Curved segments 56b promote the tendency of the stent 3 to flex longitudinally when it is subjected to bending forces such as those encountered during delivery of the stent 3 and catheter 2 through a tortuous coronary artery.

Figure 6:
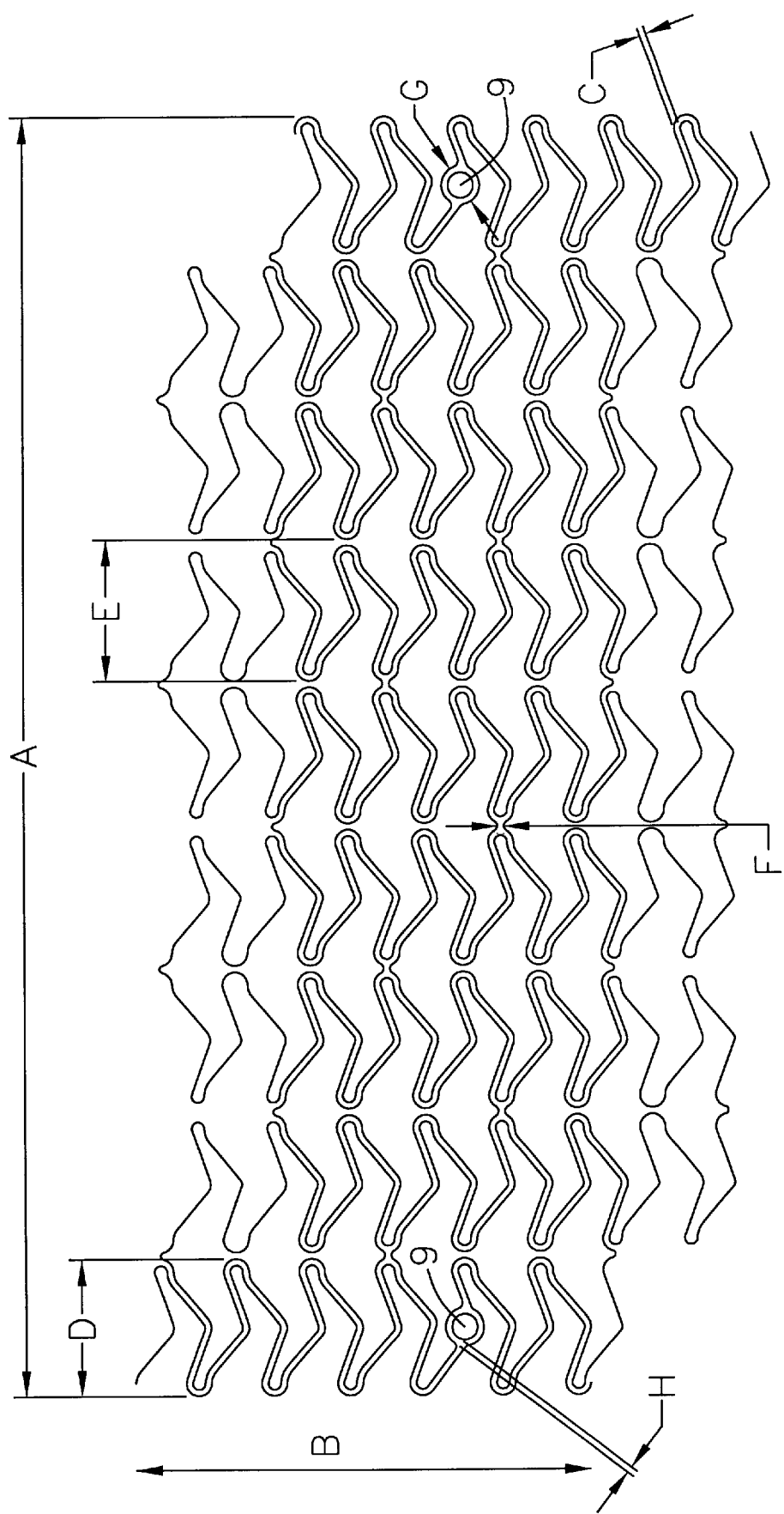
FIGS. 6–8 are flattened plan views showing stents made according to the present invention. Each of the stent patterns shown would be curved into a cylindrical shape and crimped onto the balloon catheter as shown in FIG. 1.

Referring now to FIGS. 1 and 6, a full pattern of a stent 3 for a coronary artery application is shown which is substantially the same pattern which was discussed above in connection with FIG. 2. Stent 3 has a length "A" which can be about 8 to about 42 mm (and as depicted could be about 15–25) mm for a coronary artery application although those skilled in the art will appreciate that the pattern can be configured to give many lengths. The dimension "B" refers to the circumference of the stent 3 for a coronary application which can be about 3–7 mm and gives an uncrimped diameter for the stent 3 of about 1–2 mm. The dimension "C" refers to the width of one of the rings which in this example could be in the range of about 0.08 to 0.12 mm. The dimension "D" refers to the amplitude of one of the rings and in this example could be in the range of about 0.75 to 2.5 mm. The dimension "E" refers to the peak-to-peak spacing for the rings and in this example could be in the range of about 1–3 mm. The dimension "F" refers to the width of a longitudinal connector and in this example could be in the range of about 0.06 to 0.1 mm. Radiopaque markers 9 are located at opposite ends of the stent 3 to allow the physician to precisely identify the position of the ends of the stent 3 fluoroscopically while the stent 3 is being deployed into the patient. The markers 9 can take the form of a thin gold disk set into an portion of the pattern. The markers 9 have their highest fluoroscopic visibility when looking directly down onto the flat plane of the disk and lesser visibility when looking at the edge of the disk. Therefore, the markers 9 can be aligned with each other so as to both be visible at the same intensity no matter what the rotational orientation of the stent (as shown in FIG. 6) or offset (not shown) with regard to each other to permit at least one marker 9 to always be viewed in its highly observable flat orientation. More markers can be added to those shown in FIG. 6 so that each end of the stent 3 has two or more markers in a relative offset position, which then permits one of the markers at each end to always be brightly observable no matter what rotational orientation the stent 3 is in. The dimensions "G" and "H" refer to the diameter of the radiopaque marker and the width of the portion of the ring holding the marker.

Figure 7:
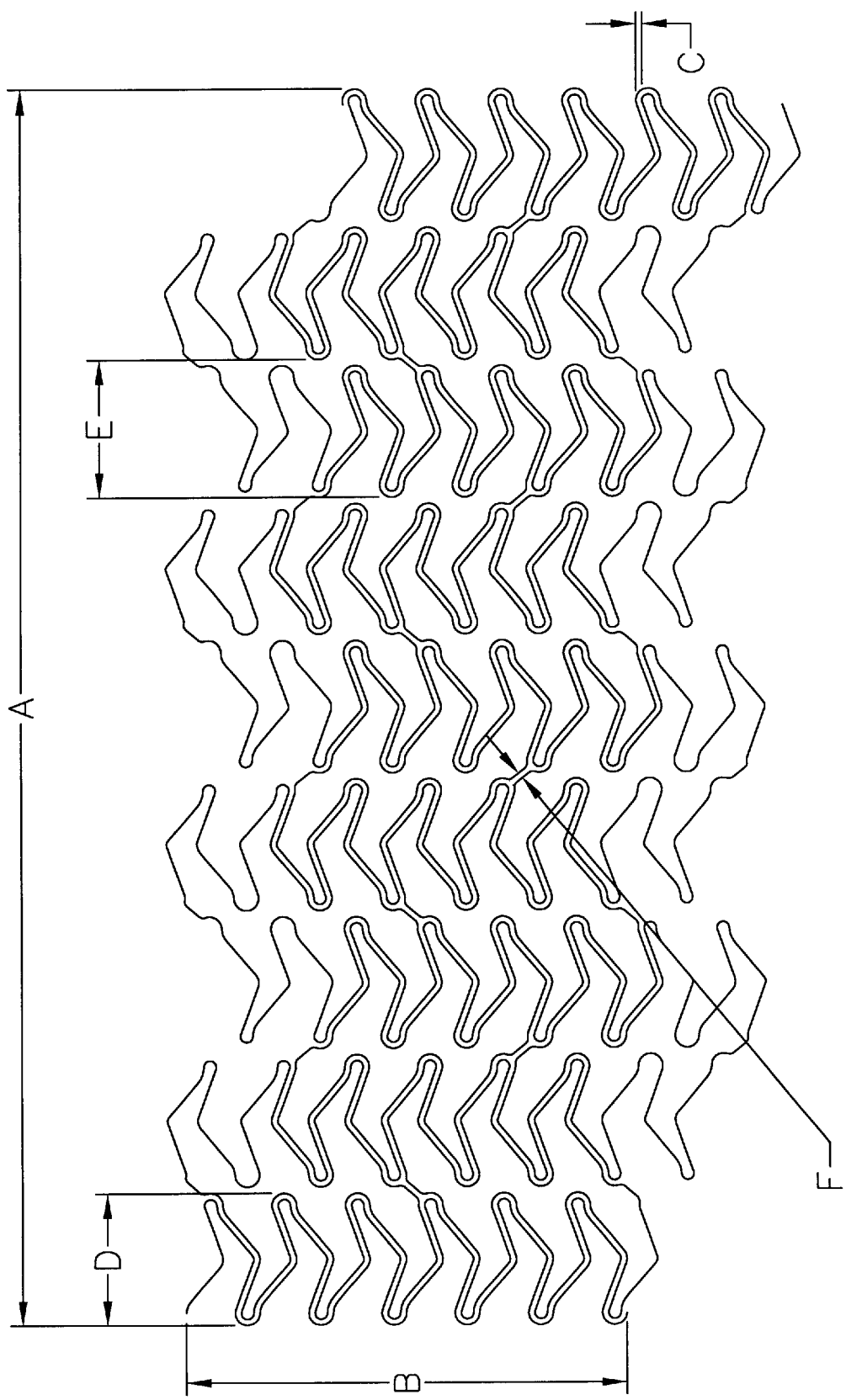

Referring now to FIGS. 1 and 7, a full pattern of a stent 3 for a coronary artery application is shown which is substantially the same pattern which was discussed above in connection with FIG. 3. Similar structures are marked with the same dimensional symbols ("A" to "F") as in FIG. 6, and the dimension ranges for the stent 3 shown in FIG. 7 are substantially as described for the stent 3 shown in FIG. 6. This stent 3 can be made by laser cutting from a tube of stainless steel or other suitable material by methods which are well known by those skilled in the art. A radiopaque marker, such as the radiopaque marker shown in FIG. 6, can be included at one or both ends of the stent 3 of FIG. 7, although it is not shown in FIG. 7.

Figure 8:
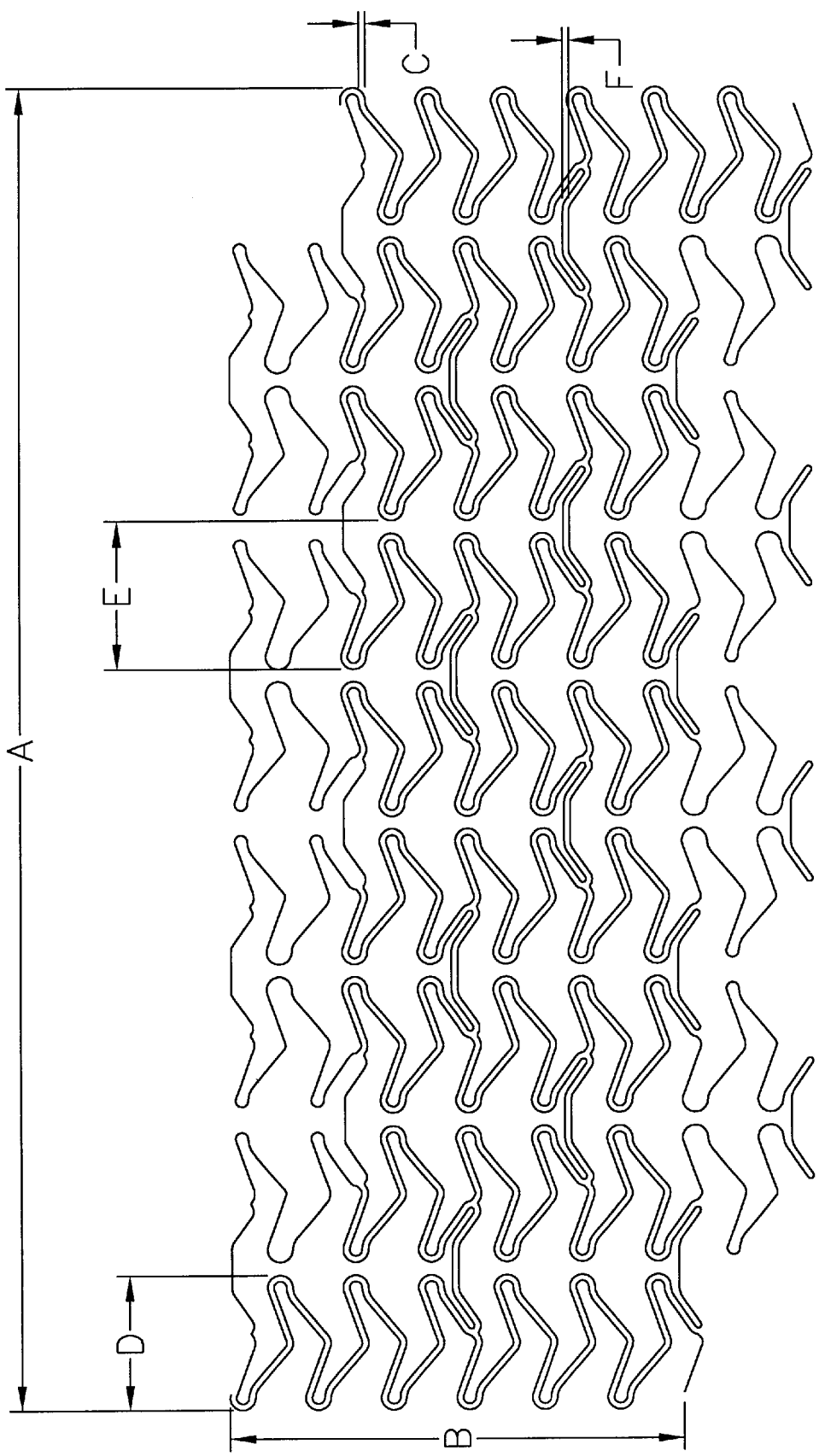

Referring now to FIGS. 1 and 8, a full pattern of a stent 3 for a coronary artery application is shown which is substantially the same pattern which was discussed above in connection with FIG. 4. Similar structures are marked with the same dimensional symbols ("A" to "F") as in FIG. 6, and the dimension ranges for the stent 3 shown in FIG. 8 are substantially as described for the stent 3 shown in FIG. 6. This stent 3 can be made by laser cutting from a tube of stainless steel or other suitable material by methods which are well known by those skilled in the art. A radiopaque marker, such as the radiopaque marker shown in FIG. 6, can be included at one or both ends of the stent 3 of FIG. 8, although it is not shown in FIG. 8.

The radially outward directed force developed by the stents according to the present invention serves two functions. One function is to hold the body lumen open against a force directed radially inward, e.g., a spasm, as well as preventing restriction of the passageway through the lumen by intimal flaps or dissections generated by, e.g., prior balloon angioplasty. Another function is to fix the position of the stent within the body lumen by intimate contact between the stent and the walls of the lumen. The outwardly directed forces must not be excessive, however, to avoid traumatization of the lumen walls by the stent.

The diameters of some preferred stents when in the compressed state for delivery to a desired location within a body lumen is typically reduced from about two to about six times the diameter of the stents when in their expanded state before compression. For example, typical stents may have a compressed external diameter of about 1 millimeter to about 3 millimeters for delivery and an expanded external diameter in a body lumen of about 3 millimeters to about 15 millimeters when released from compression in a large arterial vessel. Some preferred stents used in coronary arteries may have a compressed external diameter of about 1 millimeter and an expanded external diameter in a body lumen of up to about 6 millimeters.

In addition to ranges in diameters, it will also be understood that the stents according to the present invention can have any desired longitudinal length as required for a particular application. Furthermore, although the illustrative stents depicted in FIGS. 6–8 have a plurality of successive ring elements, it will be understood that some stents according to the present invention could be manufactured with only one ring element (in which case no longitudinal members would be required to connect adjacent support sections).

Preferred materials for fabricating stents according to the present invention include those materials that can provide the desired functional characteristics with respect to biological compatibility, modulus of elasticity, etc. Materials for both balloon-expandable stents and self-expanding stents are well-known in the art, and the device of the invention is not intended to be limited to any particular constituent material. Likewise, the manufacture of stents according to the present invention may be accomplished using any of a variety of methods that are well-known to those in the art. See, for example, U.S. Pat. No. 5,776,161 to Globerman.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. For example, although stents having one or more ring elements are described herein, it will be understood that stents manufactured according to the present invention could have any number of desired ring elements needed to obtain a stent having a desired length. Furthermore, it will be understood that the figures are schematic only, and that the relative dimensions of the various illustrated features are not intended to limit the scope of the present invention. Accordingly, the present invention is not limited to the particular embodiments which have been described in detail herein.

All patents, patent applications, publications and other documents cited in herein are hereby incorporated by reference in their respective entireties.

What is claimed is:

1. A medical device comprising:
   a catheter and a radially expandable stent mounted on the catheter, the stent comprising
      a hollow, cylindrical body comprising first and second rings extending circumferentially around the cylindrical body, each ring comprising an undulating series of peaks and valleys formed by struts connecting alternating curved peak and valley segments within the ring, the struts comprising a first curved segment curved substantially symmetrically about a single circumference of the stent such that the peaks and valleys within a ring form a nested chevron pattern; and
      at least one longitudinal connection between the first and second rings.

2. The medical device of claim 1 wherein the struts further comprise a second curved segment positioned near a curved peak or valley segment.

3. The medical device of claim 1 wherein the first and second rings are arranged in a parallel chevron pattern relative to each other.

4. The medical device of claim 1 wherein the first and second rings are arranged in an antiparallel chevron pattern relative to each other.

5. The medical device of claim 1 wherein the peaks of the first ring are longitudinally aligned with the valleys of the second ring.

6. The medical device of claim 1 wherein the peaks of the first ring are not longitudinally aligned with the valleys of the second ring.

7. The medical device of claim 6 wherein the peaks of the first ring are longitudinally aligned with the peaks of the second ring.

8. The medical device of claim 1 wherein at least one longitudinal connection is formed by a longitudinal connector.

9. The medical device of claim 8 wherein at least one longitudinal connector is curved.

10. The medical device of claim 8 wherein at least one longitudinal connector is straight.

11. The medical device of claim 1 further comprising at least one radiopaque marker.

12. The medical device of claim 1 wherein the radially expandable stent is a balloon-expandable stent.

13. The medical device of claim 1 wherein the radially expandable stent is a self-expanding stent.

14. A medical device comprising:
   a catheter and a radially expandable stent mounted on the catheter, the stent comprising
      a hollow, cylindrical body comprising first and second rings extending circumferentially around the cylindrical body, each ring comprising an undulating series of peaks and valleys formed by struts connecting alternating curved peak and valley segments within the ring, the struts comprising a first curved segment curved substantially symmetrically about a single circumference of the stent such that the peaks and valleys within a ring form a nested chevron pattern; wherein at least one strut on each of the first and second rings further comprises an inflection point positioned on a central portion of the strut; and
      at least one longitudinal connector connecting the first and second rings at the inflection points on the struts.

15. The medical device of claim 14 wherein the inflection points are positioned near the first curved segment of the struts.

16. The medical device of claim 14 wherein the longitudinal connector is curved.

17. The medical device of claim 16 wherein a portion of the longitudinal connector near the inflection point is substantially parallel to the strut.

18. The medical device of claim 14 wherein the struts further comprise a second curved segment positioned near a curved peak or valley segment.

19. The medical device of claim 14 wherein the first and second rings are arranged in a parallel chevron pattern relative to each other.

20. The medical device of claim 14 wherein the peaks of the first ring are longitudinally aligned with the valleys of the second ring.

21. The medical device of claim 14 wherein the peaks of the first ring are not longitudinally aligned with the valleys of the second ring.

22. The medical device of claim 21 wherein the peaks of the first ring are longitudinally aligned with the peaks of the second ring.

23. The medical device of claim 14 further comprising at least one radiopaque marker.

24. The medical device of claim 14 wherein the radially expandable stent is a balloon-expandable stent.

25. The medical device of claim 14 wherein the radially expandable stent is a self-expanding stent.

26. A medical device comprising:

a catheter and a radially expandable stent mounted on the catheter, the stent comprising a hollow, cylindrical body comprising first and second rings extending circumferentially around the cylindrical body, the first and second rings each comprising a plurality of closed members, each closed member comprising a peak and valley formed by a longer strut and a shorter strut connecting curved peak and valley segments, the longer and shorter struts each comprising a curved segment curved substantially symmetrically about a single circumference of the stent such that the peaks and valleys within a ring form a nested chevron pattern; circumferential connectors between the longer strut and the shorter strut of circumferentially adjacent closed members; and at least one longitudinal connection between the first and second rings.

27. The medical device of claim 26 wherein the closed members further comprises an indentation positioned on the shorter strut, such that the indentation is substantially circumferentially aligned with the circumferential connector attached to the shorter strut.

28. The medical device of claim 26 wherein the first and second rings are arranged in a parallel chevron pattern relative to each other.

29. The medical device of claim 26 wherein the first and second rings are arranged in an antiparallel chevron pattern relative to each other.

30. The medical device of claim 26 wherein the peaks of the first ring are longitudinally aligned with the valleys of the second ring.

31. The medical device of claim 26 wherein the peaks of the first ring are not longitudinally aligned with the valleys of the second ring.

32. The medical device of claim 26 wherein the peaks of the first ring are longitudinally aligned with the peaks of the second ring.

33. The medical device of claim 26 wherein at least one longitudinal connection is formed by a longitudinal connector.

34. The medical device of claim 33 wherein the longitudinal connector is curved.

35. The medical device of claim 33 wherein the longitudinal connector is straight.

36. The medical device of claim 26 further comprising at least one radiopaque marker.

37. The medical device of claim 26 wherein the radially expandable stent is a balloon-expandable stent.

38. The medical device of claim 26 wherein the radially expandable stent is a self-expanding stent.

* * * * *